United States Patent [19]

McDermott

[11] Patent Number: 4,947,844
[45] Date of Patent: Aug. 14, 1990

[54] RECEIVER/STIMULATOR FOR HEARING PROSTHESIS

[75] Inventor: Hugh J. McDermott, Kilda, Australia

[73] Assignee: The University of Melbourne, Parkville, Australia

[21] Appl. No.: 773,057

[22] Filed: Sep. 6, 1985

[30] Foreign Application Priority Data

Sep. 7, 1984 [AU] Australia .............................. PG7007

[51] Int. Cl.$^5$ ............................................. A61N 1/32
[52] U.S. Cl. .................................................. 128/421
[58] Field of Search ...................... 128/419 R, 421–422

[56] References Cited

U.S. PATENT DOCUMENTS

| | | | |
|---|---|---|---|
| 3,766,331 | 10/1973 | Zink | 128/419 R |
| 4,200,108 | 4/1980 | Weigert | 128/419 R |
| 4,400,590 | 8/1983 | Michelson | 128/419 R |
| 4,406,658 | 9/1983 | Lattin et al. | 128/419 R |
| 4,428,377 | 1/1984 | Zollner et al. | 128/419 R |
| 4,510,936 | 4/1985 | Fourcin et al. | 128/419 R |
| 4,532,930 | 8/1985 | Crosby et al. | 128/419 R |
| 4,592,359 | 6/1986 | Galbraith | 128/419 R |

Primary Examiner—William E. Kamm
Attorney, Agent, or Firm—Dennison, Meserole, Pollack & Scheiner

[57] ABSTRACT

A device for controlling stimulating currents in prosthetic devices in which a series of short spaced current pulses are delivered to electrodes with intervals between the pulses of zero current having a duration longer than that of each spaced pulse, the waveform of the stimulus current comprising a series of said spaced pulses of one polarity followed by an equal number of said spaced pulses of opposite polarity whereby the sum of all of the electrical charge transferred through each electrode is approximately zero at the end of a stimulating current waveform. In a hearing prosthesis in which bipolar pairs of electrodes are used to stimulate hearing nerves, the spaced pulses are delivered cyclically to the bipolar pairs of electrodes whereby the spaced pulses are delivered to one electrode pair during the zero current periods of the spaced pulses delivered to another electrode pair whereby the electrical stimulation caused by said electrodes is substantially simultaneous.

8 Claims, 7 Drawing Sheets

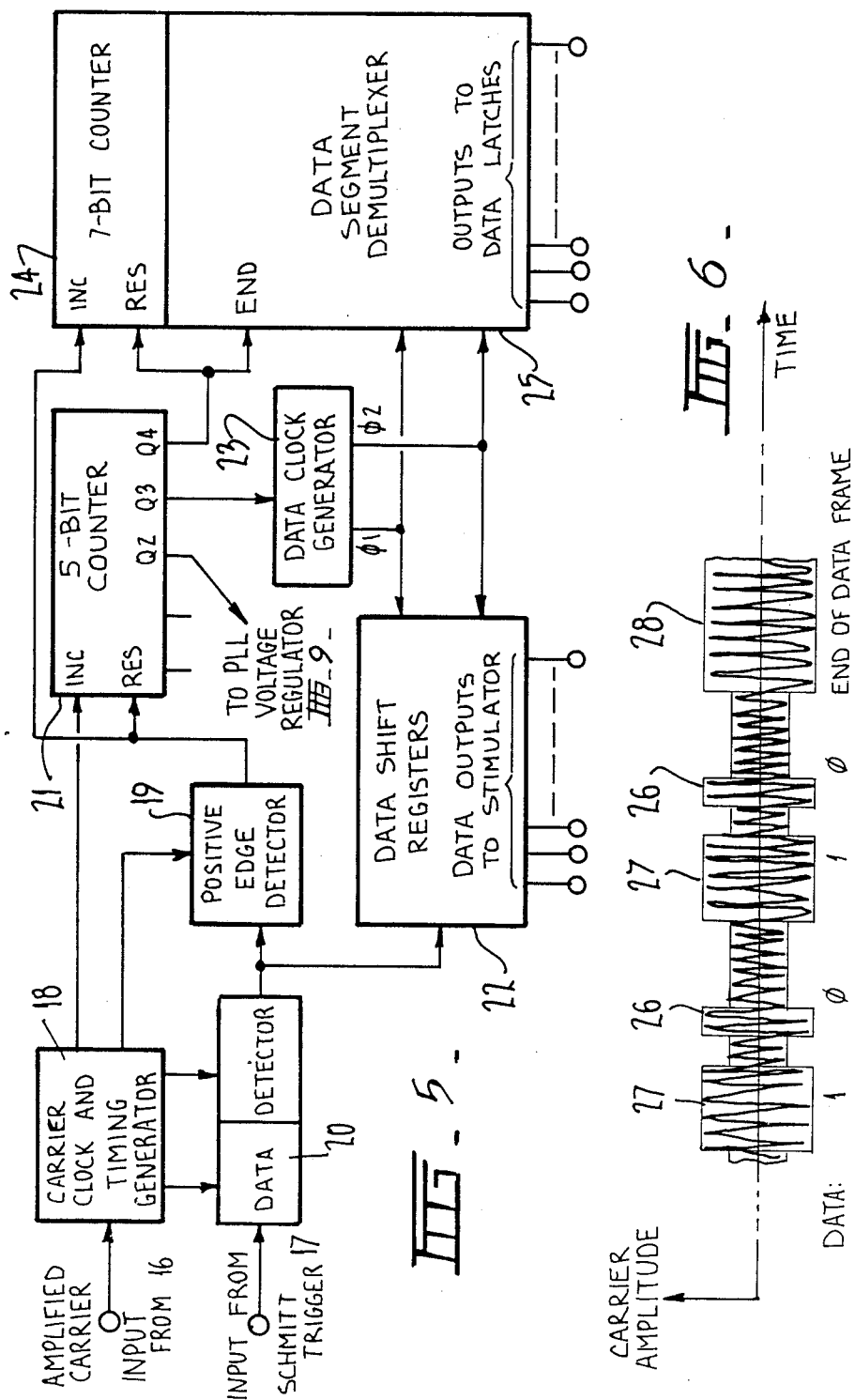

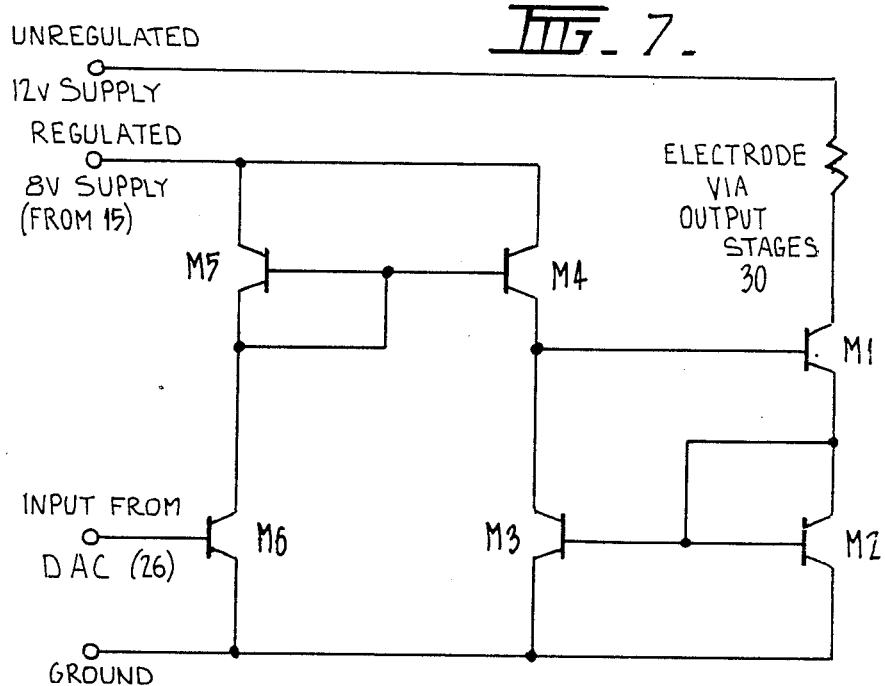
FIG_7_
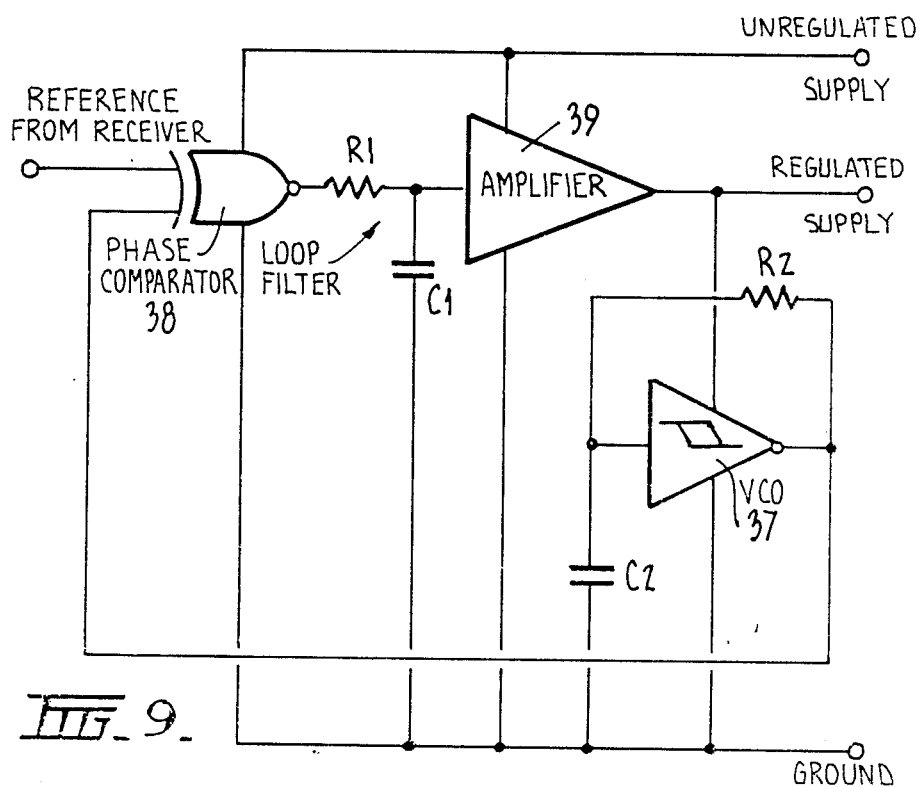
FIG_9_

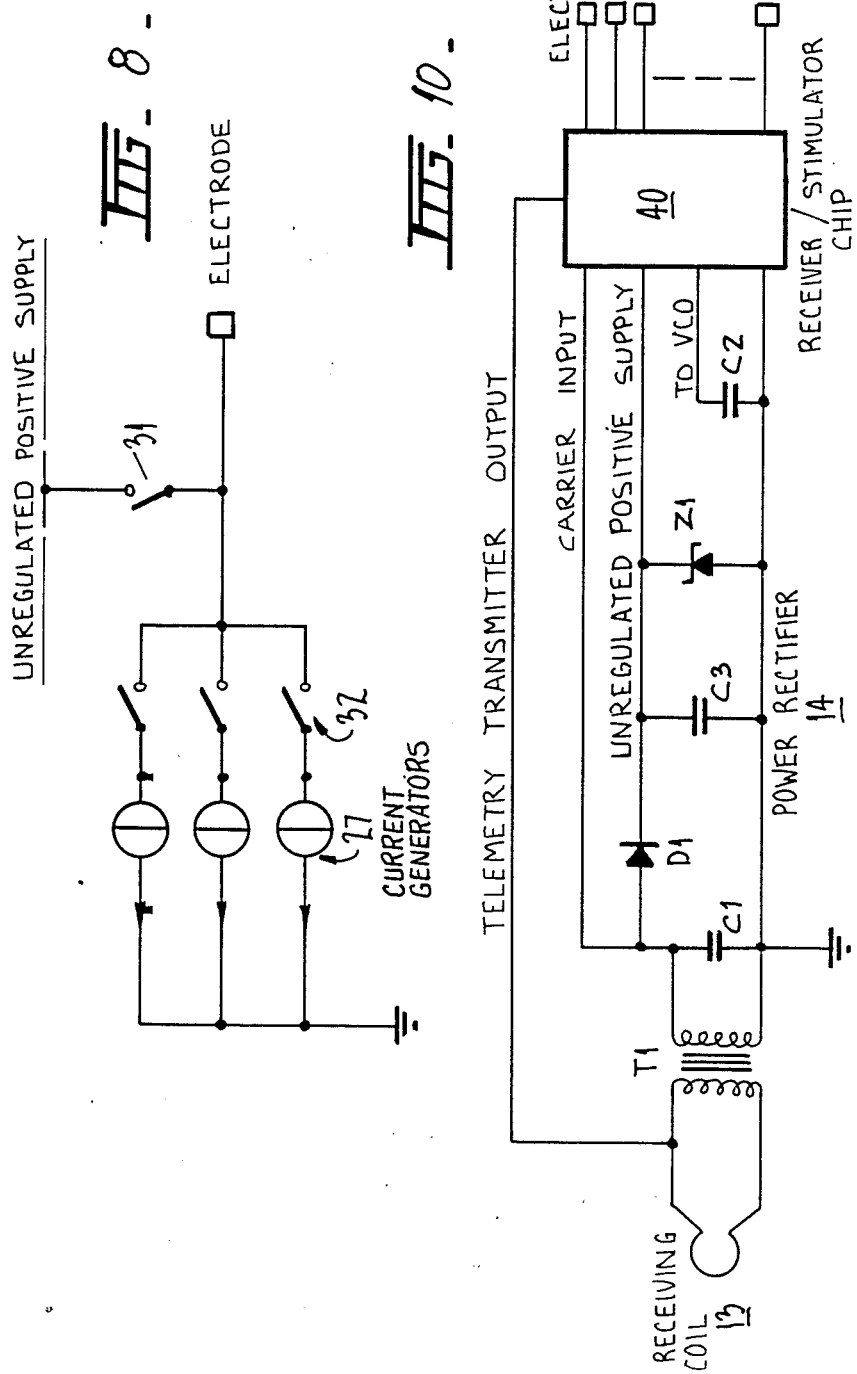

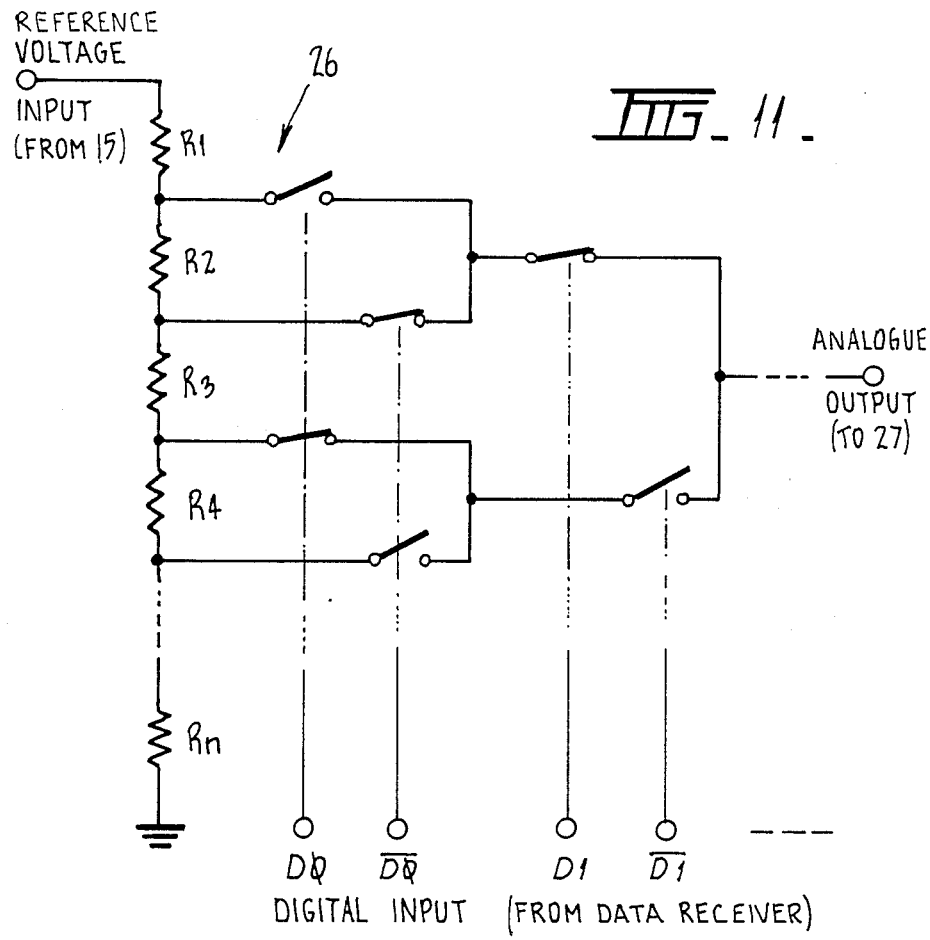
FIG_11.
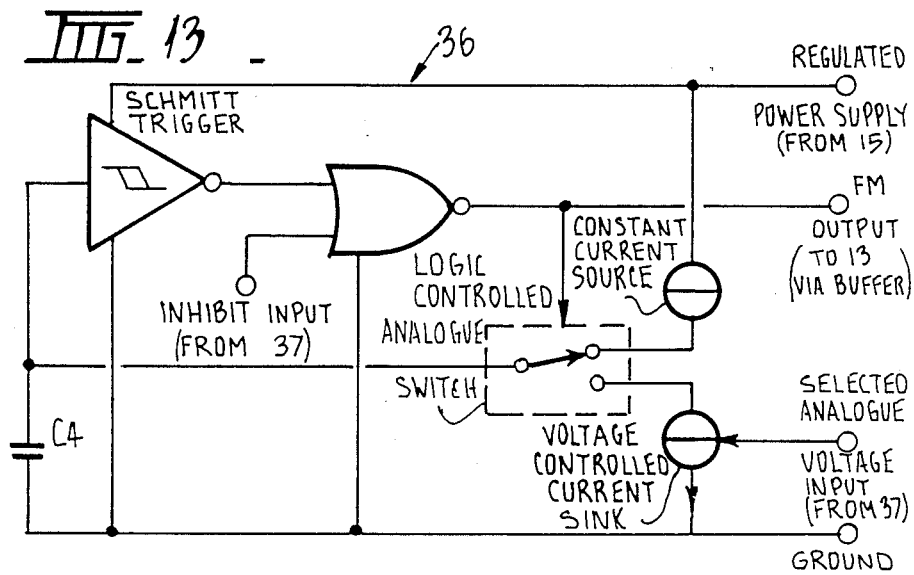
FIG_13.

RECEIVER/STIMULATOR FOR HEARING PROSTHESIS

FIELD OF THE INVENTION

This invention relates to the control of stimulating currents in prosthetic devices. More particularly the invention relates to receiver/stimulator means for use in hearing prosthesis intended to restore some hearing to the profoundly or totally deaf and in other biomedical applications, especially those involving electrical stimulation of nerves.

BACKGROUND OF THE INVENTION

In our U.S. Pat. Nos. 4,267,410 Forster et al, 4,441,202 Tong et al. and Australian Patent Applications Nos. AU-B 41061/78. AU-B 59812/80 and AU-A18194/83, we have described various aspects of a hearing prosthesis system of the above type. In the preferred realizations of this system. the implanted hearing prosthesis comprises three basic components: a receiver/stimulator implanted in the mastoid process, an electrode array implanted in the scala tympani of the inner ear, and the interconnection between the receiver/stimulator and the electrode array. The receiver/stimulator receives a radio frequency signal from an external transmitter demodulates and decodes this signal, and generates electric current which is delivered to the electrodes according to the decoded information.

Investigations of the receiver/stimulator determined that it would be advantageous to have a greater degree of control over the stimulation applied by the array of electrodes. In particular greater control over the distribution of currents along the length of the scala tympani is important because it has been established in psycophysical studies that the timbre of the hearing sensation is closely related to the current distribution.

The preferred form of electrical stimulation utilized in existing hearing prostheses and other neural stimulators is the biphasic constant-current pulse exemplified in FIG. 1. The two phases or halves of this pulse 1 and 2 have equal durations and equal current levels. The direction of current flow in the second phase 2 is opposite to that in the first phase 1. There may be an interphase interval 3 in which no electrode current flows. One important characteristic of this signal is that the amount of charge contained in the second phase of the pulse is exactly equal and opposite to that contained in the first phase. This is because it is essential that the total of all the charge transferred through any electrode by the time of the end of each biphasic current pulse closely approximates zero in order to ensure the safety of long-term electrical stimulation. The duration of the pulse is typically somewhat less than 1 ms.

In the past, hearing prostheses have used one of the following three modes of stimulation: monopolar, common-ground or bipolar stimulation. To produce neural excitation with monopolar stimulation, one or more electrodes implanted in the scala tympani conducts biphasic current pulses such that the total current flows through a single ground electrode located at a remote site. For common-ground stimulation, electrodes interspersed between the active scala tympani electrodes are connected to ground and conduct the current supplied by the active electrodes. In bipolar stimulation, biphasic constant-current pulses are passed between two ala tympani electrodes. A number of such bipolar electrode pairs may be used simultaneously in a hearing prosthesis. Of the three modes of stimulation, it is generally accepted that the bipolar mode provides the greatest degree of control over the distribution of currents in the scala tympani. However, it has been found to be impractical to achieve simultaneous stimulation of two or more electrodes while still achieving a zero charge balance since independent current sources are required for each electrode required to apply simultaneous stimulation and it is impractical to control such current sources to achieve the required degree of charge balance.

It is one specific object of the present invention to ensure that the sum of all the charge transferred through any electrode is as close as fractical to zero at the end of a stimulating current pulse even when several bipolar electrode-pairs are stimulating at discrete sites in the scala tympani substantially simultaneously or quasi-simultaneously. In the present specification, the term "quasi-simultaneously" refers to stimulation which appears to the nerves being stimulated to be simultaneous.

It has been shown in various physiological studies that the amplitude of the gross neural response (i.e. the auditory brainstem response) to an electrical stimulus is determined mainly by the amount of charge delivered to the electrodes during one phase of the biphasic stimulus pulse. The shape of the current waveform producing this charge transfer is relatively unimportant in nerve stimulation; only the amount of charge delivered to the electrodes needs to be accurately controlled, provided that the duration of the electrical stimulus is short (i.e. less than approximately 1 ms). This general characteristic has been verified for Pulsatile current waveforms having duty cycles in the range of 30°-100°.

The present invention makes use of this fact in enabling the presentation of electrical stimulation to several scala tympani sites substantially simultaneously or quasi-simultaneously. Each bipolar pair of stimulating electrodes is made to conduct a series of short, discrete elemental constant-current pulses which in total approximates the effect of a single conventional biphasic constant-current pulse of the type shown in FIG. 1.

Thus, in its broadest form the invention provides a means for controlling currents delivered to electrodes for stimulating nerves in prosthetic applications, said current control means being characterized in that current is delivered to each electrode or to each bipolar pair of electrodes in a series of short elemental pulses, each elemental pulse being separated from the next by an interval of zero current which has a longer duration than an elemental pulse. The waveform of the stimulus current comprises a series of said pulses of one polarity followed by an equal number of said pulses of opposite polarity whereby the sum of all the electrical charge transferred through each electrode is approximately zero at the end of a stimulating current waveform. In this way elemental current pulses applied to each electrode or each pair of electrodes which are stimulating simultaneously are preferably delivered cyclically such that elemental pulses delivered to one electrode are interleaved in time with those delivered to any other electrodes, thereby enabling the use of a single current source. Even though the electrodes are not stimulating in a truly simultaneous manner, the capacitance of the system means that it appears to the nerves that they are in fact being stimulated simultaneously so that all of the advantages of simultaneous stimulation are achieved.

The elemental current pulses may be either rectangular constant-current pulses or pulses whose amplitudes vary continuously in time, provided that they are interspersed with zero-current intervals as described.

In one specific form, the present invention provides in a receiver/stimulator for a hearing prosthesis comprising means for receiving a transmitted data signal, means for decoding the received signal, means for generating and delivering several independent current signals to a selected subset of stimulating electrodes, configured as a number of bipolar pairs, according to the decoded information, the improvement comprising means for controlling said current signals to cause said bipolar pairs to conduct a series of short elemental constant-current pulses each separated by zero-current intervals longer than each elemental pulse. said series of elemental pulses being divided into two halves having opposite current direction whereby the sum of the charge transferred through each of the selected bipolar electrode pairs is exactly zero when the delivery of the current signals is complete.

BRIEF DESCRIPTION OF THE DRAWINGS

One preferred form of the electrical circuit which generates the interleaved series of elemental current pulses defined above will now be described in further detail with reference to the accompanying drawings in which:

FIG. 5 is a block diagram of the receiver included in FIG. 4:

FIG. 6 is a graph showing the data carrier waveform used in the present embodiment;

FIG. 7 is a circuit diagram of the voltage controlled current generators included in FIG. 4;

FIG. 8 is a simplified schematic of the output stage of FIG. 4;

FIG. 9 is a circuit diagram showing one preferred voltage regulator for use in the circuit of FIG. 4;

FIG. 10 is a schematic circuit diagram showing the implanted electronics.

FIG. 11 is a schematic circuit diagram showing the principal of operation of the digital to analogue convertor:

FIG. 13 is a schematic circuit diagram of the telemetry transmitter.

DESCRIPTION OF THE PREFERRED EMBODIMENTS

Figure 1:
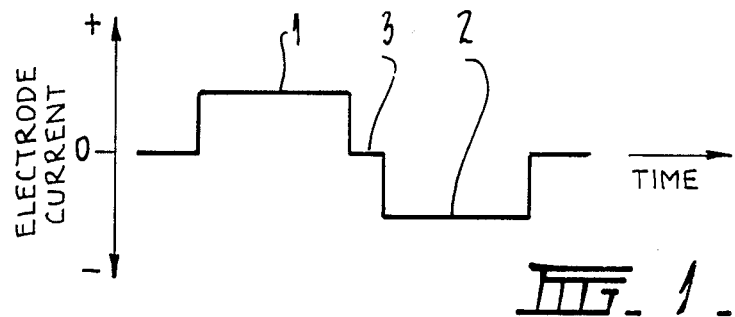
FIG. 1 is a graph of electrode current against time showing a typical biphasic constant-current pulse waveform.
Figure 2:
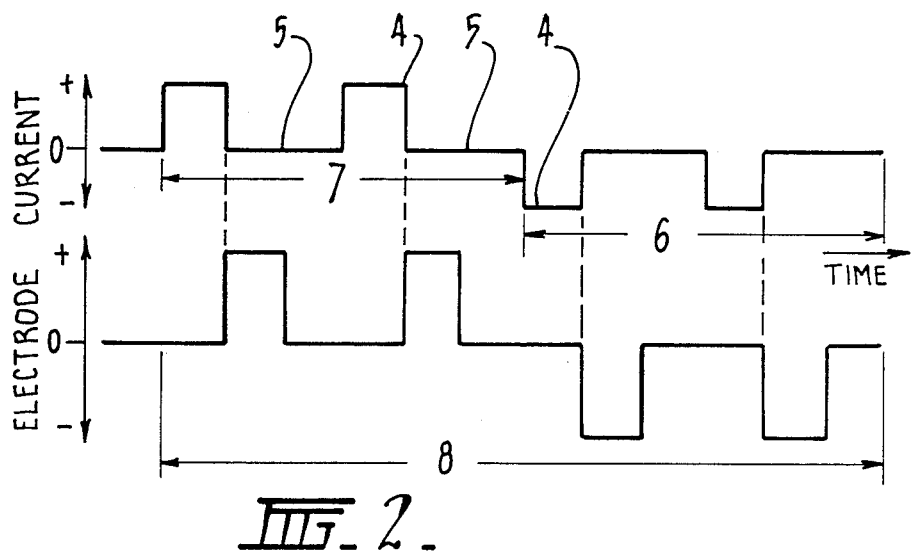
FIG. 2 is a graph of electrode current against time showing a stimulus current waveform embodying the invention.

Referring firstly to FIG. 2, the new stimulus current waveform embodying the invention will be seen to comprise a series of elemental current pulses including a number of pulses of equal duration 4 separated by zero-current intervals preferably of length several times the pulse duration 5. The second half of the series of pulses 6 has the direction of current flow through the electrodes reversed relative to the first half 7, while the duration of each elemental pulse is the same. The number of elemental pulses in the second half of the series exactly equals that in the first half. This ensures that the sum of all the charge transferred through the electrodes approximates zero at the end of the series of pulses.

The timing of the series of pulses must be controlled so that while current is flowing through one bipolar electrode pair, no other electrodes are conducting current. When several electrode pairs are presenting stimulation quasi-simultaneously, the current pulses are delivered to the electrodes cyclically so that the series of pulses are interleaved in time and never overlap. Stimulating current is never allowed to flow through more than one electrode-pair at a time. In FIG. 2, the second waveform 8 is a series of elemental current pulses stimulating quasi-simultaneously with the first according to this technique.

Figure 3:
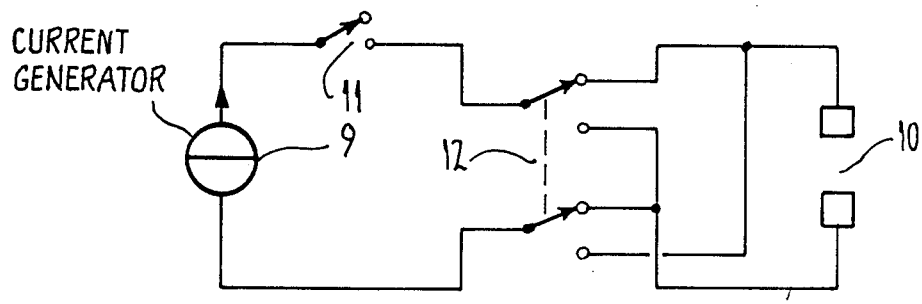
FIG. 3 is a schematic circuit diagram showing a switching arrangement suitable for achieving the waveform of FIG. 2.

The advantage of this form of stimulation over previous techniques is that it obviates the need for a highly accurate, precisely controlled bilateral current generator for each stimulating electrode. Current generators which can produce exactly-matched currents flowing through two electrodes in opposite directions over required two-decade range of electrode current cannot easily be miniaturized to the extent necessary for implantable hearing prostheses. Instead, this invention requires only one unilateral current generator for each quasi-simultaneously-stimulating bipolar electrode pair. This is shown in the schematic diagram of FIG. 3. The current generator 9 delivers current to the electrode pair 10 through switches 11, 12. Switch 11 defines each elemental current pulse; while it is open, an elemental current pulse may be delivered to an electrode pair by another current generator (not shown). Switch 12 determines the direction of current flow through the electrodes. At the end of the first half of the series of elemental current pulses, switch 12 changes over to deliver the second half in the opposite direction.

Figure 4:
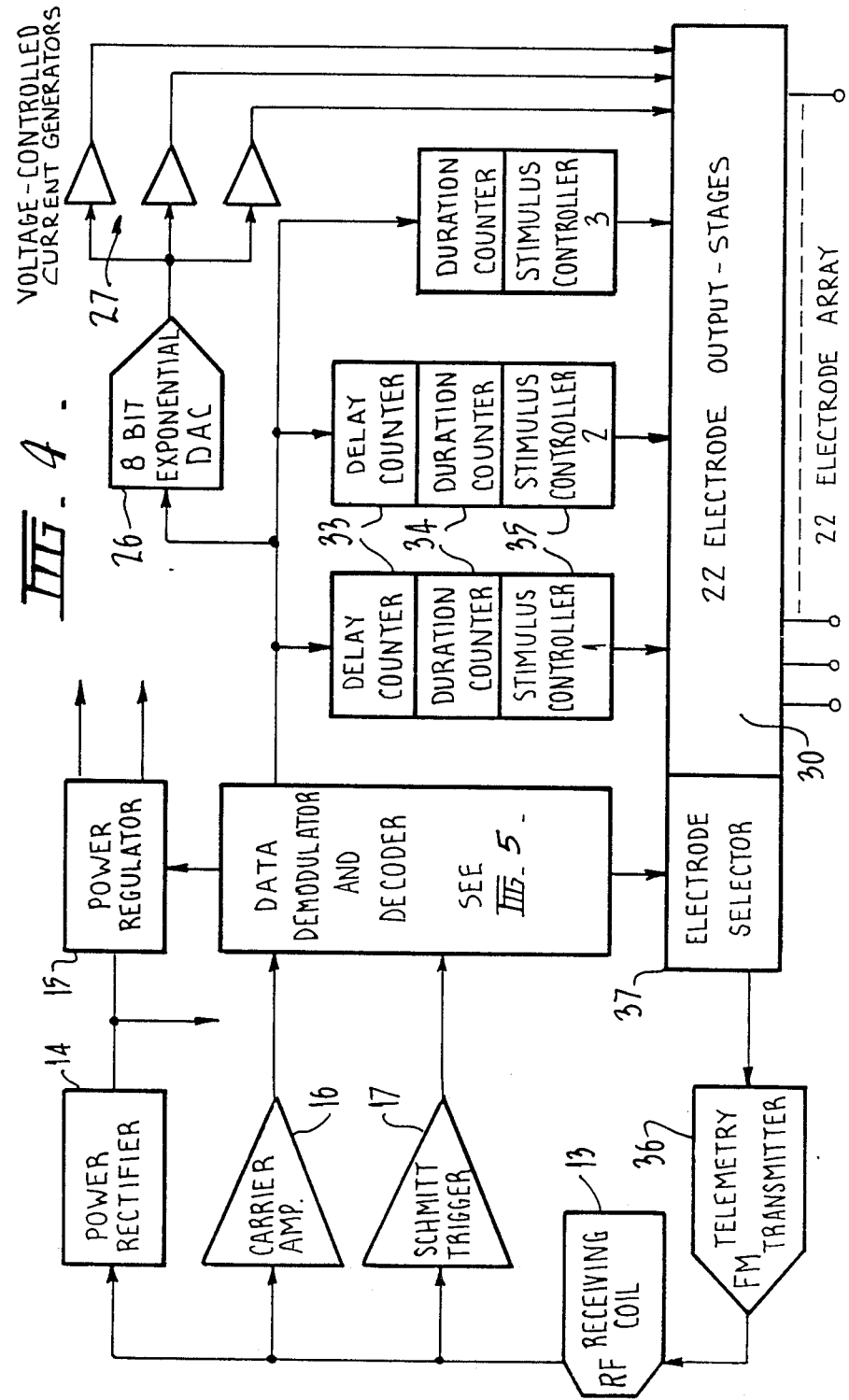
FIG. 4 is a block diagram of a receiver/stimulator circuit embodying the invention.

The block diagram of FIG. 4 shows one design of a receiver/stimulator system embodying the major aspect of the invention described above. Because it is so important to minimize the size and power consumption of an implantable device, nearly all of the circuitry described below resides on a single CMOS large scale integrated circuit. FIG. 10 shows how this chip is incorporated into the total implantable receiver/stimulator system. In FIG. 10. $T_1$ is a tuned impedance transformer which couples signals from the receiving coil 13 to the carrier input of the chip 40. As the signals received will include negative voltages (with respect to the system ground), the electrostatic discharge protection on the carrier input to the chip does not have a reverse-biased diode connected to ground, as is usual for a CMOS chip. Instead a pMOS transistor (not shown) connected in the punch-through mode provides protection for the chip against large negative voltages. D1 and C3 rectify and filter the received carrier to provide the chip's main unregulated power supply. Z1 is a zener diode which protects the chip against excessive voltages. C2 sets the level of the chip's internal regulated voltage as described below. Outputs from the chip include the output from the telemetry transmitter 36 (FIG. 4) which is connected to the receiving coil 13, and the twenty two connections to the electrode array.

Digital control signals and electric power are transferred from an external speech-processor/transmitter (not shown) of the general type described in U.S. Pat. No. 4441202 Tong et al. and as manufactured by Nucleus Limited of 1 Woodcock Place, Lane Cove, 2066, New South Wales, Australia under the type number WSP1, and are received by the RF receiving coil 13. The data produced by the speech-processor modulates a radio frequency (RF) carrier, whose frequency is 2.5 MHz, at a rate of 16 carrier cycles per data bit, or approximately 160 kbit/s. A carrier frequency of 2.5 MHz was chosen to maximize the data transfer rate without incurring unacceptable losses in the transcutaneous power transfer. The data is impressed on the carrier by a form of pulse-width modulation exemplified in FIG. 6: a short burst of high-amplitude carrier (1–8 cycles) signals a logical '0' 26, while a longer burst (9–15 cycles) represents a logical '1' 27. The carrier amplitude is reduced to a small (non-zero) value for the remainder of each 16-cycle bit period, so that the carrier can be used as a continuous frequency reference in the voltage regulator circuit 15, as explained below. At the end of a complete sequence of ninety one data bits, which specifies up to three different though simultaneously-generated electrode current pulses in a format to be described, the carrier is continuously transmitted at maximum amplitude 28. This ensures that the implant receives most power when it is most needed: during nerve stimulation. When stimulation is complete a new data frame may be transmitted.

The received data is demodulated by means of the technique shown in block diagram form in FIG. 5. The carrier is amplified and converted to a binary timing signal which is continuously present while the speech-processor is transmitting. The carrier amplifier 16 in FIG. 4) is a simple low-gain circuit consisting of a cascade of digital inverters. The Schmitt trigger 17 determines whether each individual cycle of carrier was transmitted at a low or high amplitude. The threshold of the Schmitt circuit 17 tracks the unregulated supply voltage which is almost equal to half the peak received carrier amplitude. This optimizes the ability of the receiver to distinguish between bursts of carrier transmitted at low and high amplitudes. The timing signals from the carrier clock and timing generator 18 FIG. 5) clock the digital positive-edge detector 19 which compares consecutive outputs of the Schmitt trigger 17 sampled at the centre of each positive carrier cycle and stored in the data detector 20. This locates the start of each data bit. The 5-bit counter 21, reset at the start of the bit, transfers the data from the data detector into the data shift-registers 22 after eight carrier cycles by means of the data clock generator 23. This type of receiver is tolerant of variations in the number of cycles of high-amplitude carrier received for each data bit. The shift-registers, clocked by the data clock generator, convey the received data to the stimulator section of the implant.

The end of a data frame is signalled when the 5-bit counter 21 indicates that the carrier has been at a high amplitude continuously for more than twenty four cycles. Stimulation is disabled by means of an inhibitory signal supplied to the stimulus controllers (described later). however, unless the number of data bits received since the end of the last data frame was detected is exactly equal to ninety one at that time. The 7-bit counter 24, incremented at the start of each data bit, contains the number of data bits received. If the received signal is excessively distorted, or synchronization has been lost, the stimulator cannot go ahead and generate electrode current pulses with spurious parameters derived from an incomplete data frame.

The 7-bit counter is also used to separate the received data frame into a number of segments which control different aspects of the three different stimuli. This is done by the data segment demultiplexer 25, which stores the data in latches located in the stimulator section of the system. As already mentioned, this design can generate up to three quasi-simultaneous stimuli. The same principles of operation could of course be extended to a greater number of quasi-simultaneous stimuli, but this device will provide a significant movement over existing ices in the range of hearing sensations that can be elicited in an implanted patient. Each stimulus is a series of elemental constant-current pulses, as described above and shown in FIG. 2. applied to any one pair of electrodes. One stimulus always starts immediately after the data frame has been completely decoded while the other two each have a variable delay time relative to the end of the data frame. The length of the delay is adjustable from 0 to 609.6 us in 4.8 us steps. The overall duration of each phase of each of the three stimuli can be set to any value in the range of 0 to 302.4 us, again in increments of 4.8 us. A clocking signal with a period of 4.8 us is conveniently generated by digital division of the received carrier. The range and precision of the stimulus parameters have been found to be more than adequate in psychophysical experiments into auditory nerve stimulation. The timing of each series of elemental current pulses is directed by the three stimulus controllers, which will be described later.

The amplitude of each series of elemental current pulses is an exponential function of the value of a corresponding 8-bit segment of the data frame. This characteristic is chosen so that the loudness ratio resulting from an incremental change in the current level is constant across the entire range of stimulus current amplitudes. The exponential digital-to-analogue conversion is performed by an 8-bit exponential digital-to-analogue convertor (DAC) 26 containing a network of transistor switches which select a voltage from a string of unequal resistors to $R_1$ as shown schematically in FIG. 11. This type of DAC is described in Hamade, A.R.: "A single-chip all MOS 8-bit A/D converter", IEEE J. Solid-State circuits, vol. sc-13. pp 785–791. The resistor string 26 with the required variation in resistance over its length is formed on the receiver/stimulator chip with a diffusion region having an irregular geometric pattern. This type of digital-to-analogue converter DAC) guarantees that the electrode current is monotonically related to the value of the amplitude data segment. This arrangement simplifies the translation of acoustic amplitudes into stimulus current levels, which is accomplished in the speech-processor.

Because it is desirable to ensure that the relationship between the amplitude data segments and the resulting electrode current levels be matched for the three independent stimuli specified in each data frame, there is only one DAC in the receiver/stimulator circuit. The three amplitude data segments are supplied to the DAC 26 in sequence as soon as they are received. The DAC output voltages generated by the first two data segments are stored on two integrated capacitors (not shown). while the third voltage is available from the DAC throughout the stimulation interval.

These three analogue voltages are transformed into electrode currents by the three voltage-controlled current generators 27. Common-centroid circuit layout techniques. which cancel first-order mismatches in semiconductor device characteristics, assist in matching their transfer functions over the full range of electrode currents (approximately 20 uA−2 mA). An output resistance of greater than 500 kohm is ensured by the use of very large transistors in a Wilson current sink configuration M1, M2, M3 (see FIG. 7). An improvement in the output voltage compliance of this circuit is possible by replacing M1 with a native-mode MOS transistor, which has a near-zero threshold voltage. The outputs of these circuits are routed through the twenty two output-stages 30 which drive the array of twenty two separate intracochlear electrodes. This is the largest number of electrodes which it is convenient to control using presently-available technology The output-stages decode six 5-bit data segments from the received data frame. These segments determine which electrode is to be the current source and which the current sink for each stimulus Each output stage (see FIG. 8) contains a network of low-resistance analogue switches which connect the current generators 27 to the appropriate electrodes under the direction of the three stimulus controllers 35. Any electrode which is specified to be a current source is connected to the unregulated positive supply voltage by switch 31, while a current sinking electrode is connected to one of the voltage-controlled current generators by one of switches 32. These switches 31,32 are gated on and off by the stimulus controllers as described below in order to delineate each elemental stimulus current pulse.

The delay counters 33 in the stimulus controllers 35 are loaded with the received delay data segments and commence counting at a rate of one-twelfth of the RF carrier frequency (i.e.: approximately 208 kHz as soon as the end of a data frame is detected. When the delay counter overflows, the controller starts generating the series of elemental electrode current-pulses, via the relevant outputstages, with each pulse having a duration of approximately 1.6 us, and loads a counter 34 with the duration data. The duration counter 34 is clocked at the same rate. When the duration counter overflows, the stimulus is stopped for an interval of approximately 40 us. This interphase non-stimulating interval has been shown to reduce the threshold of auditory nerve fibres to electrical stimulation. Its length is not critical. The series of elemental pulses then continues with the direction of the electrode current flow reversed via switches 31,32 in the relevant outputstages. while the counter 34 is reloaded with the same data. The subsequent duration counter overflow causes the controller to turn off the appropriate output-stages thus completing the generation of a stimulus of the type shown in FIG. 2. The interval 5 between consecutive current pulses on each electrode-pair is approximately 3.2 us, allowing three quasi-simultaneous stimuli with elemental pulses of 1.6 us duration to be generated with adequate overall time-domain resolution.

Figure 12:
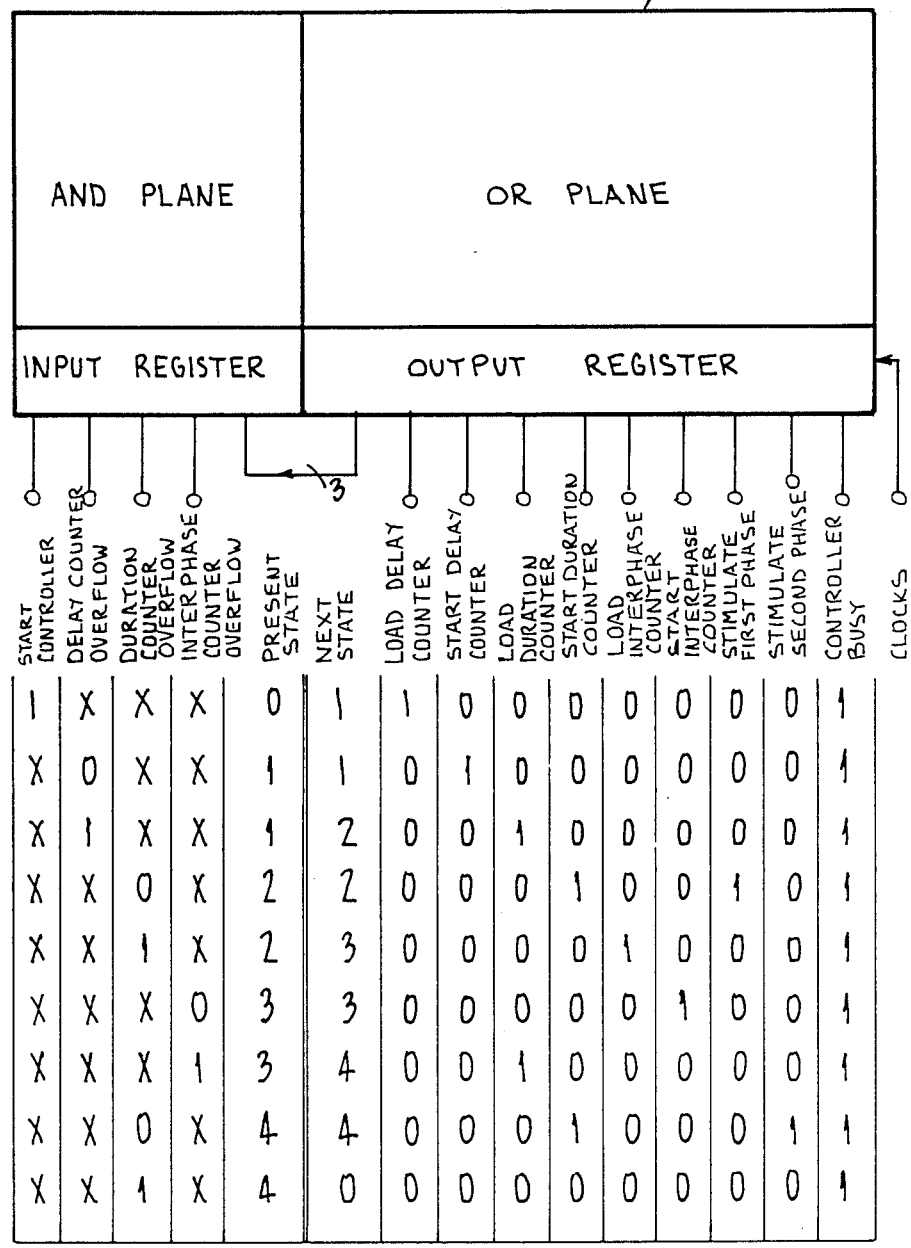
FIG. 12 is a block diagram of the stimulus controller including a state table which explains its basic operation.

The sequence of operations performed by the controller is directed by a finite state machine which is based on a programmable logic array. FIG. 12 shows a block diagram (not including counters) and state table for the state machine. The design of this unit follows the methodology described in Mead, C.A. and Conway. L.A.: "Introduction to VLSI Systems, Reading: Addison-Wesley, 1980, pp 79–90.

Long-term physiological studies have shown that it is most important to maintain exact symmetry in the stimulating current pulses. The biphasic constant-current pulse has the effect of placing the electrodes, and the fluid surrounding them, into a similar electrochemical state after the stimulus as had existed before it. In this design, the reversibility of the electrochemical reactions at the electrodes is further promoted by connecting all the electrodes together (and to the positive supply voltage) with the analogue switches 31 whenever the stimulator is inactive.

If the electrode impedance is high and/or the supply voltage to the stimulator is low while a high level of electrode current is being generated, it is possible for the voltage on a current sinking electrode to enter a range (below approximately 2V) in which the current generator cannot properly control the electrode current. In order to detect this condition externally after the receiver/stimulator has been implanted, this design incorporates the frequency-modulated low-power telemetry transmitter 36 which can telemeter one electrode voltage, measured during stimulation, to an external receiver for monitoring and analysis. Each data frame contains one 5-bit segment which causes the electrode selector 37 to connect one electrode or one of several critical voltage nodes in the receiver/stimulator circuit to the input of the transmitter. The selected voltage is referred to the system ground voltage by the transmitter. If none of these inputs is selected, the transmitter is disabled to reduce power consumption. The transmitter comprises a voltage-controlled oscillator, as shown in FIG. 13, with a free-running frequency of approximately 1 MHz. This frequency is selected to minimize power consumption while providing adequate bandwidth for the transmitted voltage measurement. The output of the oscillator is coupled to the implant's receiving coil. It may be detected by an external receiving antenna located near the speech-processor's transmitting coil, and demodulated to recover the selected voltage waveforms by means of a conventional phase-locked loop or similar circuit. This telemetry system makes possible the testing of the receiver/stimulator while the auditory nerve is actually being stimulated, and helps to ensure that the implant is operating safely in the long term. It is anticipated that it may also prove useful in researching the time-dependent electrical properties of the electrodes, and perhaps may be able to telemeter the very weak electrical signal that is produced by the nerves in response to a stimulus.

The power rectifier 14 of FIG. 10 processes the radio frequency signal received from the speech-processor to provide the main power supply for the receiver/stimulator. Because there is no way of ensuring that the speech-processor's transmitting coil is properly aligned with the implanted receiving coil, the main supply voltage to the chip may vary from zero up to approximately 12 V. For the logic circuits any supply above approximately 3 V is adequate, but the DAC, electrode-current generators, and telemetry circuit all require a well-regulated supply. A novel technique has been developed to overcome this problem.

The power regulator 15 is a modified phase-locked loop (PLL) circuit (see FIG. 9). It comprises a voltage-controlled oscillator (VCO) 37, Phase comparator 38, low-pass loop filter R1/C1 and amplifier 39. The VCO is based on a Schmitt trigger: frequency control is effected by means of the supply voltage to this circuit, there being no separate connection to the main unregulated power supply. This means that the VCO frequency is dependent on three main parameters: the circuit temperature, which affects various critical device electrical parameters, the value of a specially-selected capacitor C2 and the VCO's control voltage.

In this application the circuit temperature is unlikely to vary significantly because the heat dissipated by the implant is small and its environment (the human body) is thermally well-controlled. The capacitor C2 (see FIG. 10) is chosen during implant assembly to set the regulated voltage exactly to the correct level, approximately 7V. The phase comparator, which is similar to an exclusive-NOR logic gate, continuously compares the VCO frequency with that of a reference signal derived from the receiver. To reduce the VCO's power consumption without causing excessively long PLL settling times, the reference signal is at one eighth of the carrier frequency (approximately 310 kHz) The output of the phase comparator is filtered by R1/C1 and amplified and becomes the control voltage to the VCO, thus phase-locking the VCO to the transmitted RF carrier signal, which is controlled by an extremely stable crystal oscillator located in the speed-processor. The VCO control voltage is thereby precisely determined by the carrier frequency. The amplifier is designed to be able to supply power to the DAC and electrode-current generators as well as the VCO, so that these circuits also receive an extremely stable supply voltage. The same voltage is used by the telemetry transmitter as a reference to ensure its stability.

A second phase comparator, which also compares the VCO and reference signals, disables the stimulus controllers if the VCO is not locked to the reference signal. Normally the unlocked condition would indicate that the implant's supply voltage is too low (below approximately 8V). and it would be dangerous to attempt to stimulate in that case. This lock detector also provides a general reset signal for the stimulator logic, so that it can be placed into a predictable quiescent state when power is first applied to the device and before the PLL has settled.

Since this voltage regulator supplies both the DAC and electrode current-generators, varying the regulated voltage causes a corresponding and predictable variation in the electrode currents. It is therefore possible with this design to produce continuously-varying electrode currents by frequency-modulating the carrier signal transmitted from the speech-processor. To utilize this additional aspect of the invention, all that is necessary is to replace the crystal controlled oscillator in the speech-processor with a variable-frequency oscillator. Electrode current levels can then be steplessly controlled continuously in time by varying the frequency of the carrier signal.

It should be understood that above described embodiment is illustrative only and none of the specific circuit arrangements described is essential to the invention. For instance, the power regulator 15 may be replaced by any suitable voltage source.

What is claimed is:

1. In a prosthetic device including several electrodes by means of which electrical stimulation is achieved, the improvement comprising, means controlling the delivery of electrical stimulus current to each of said electrodes in a series of spaced pulses, each spaced pulse being separated by an interval of zero current which has a duration longer than each spaced pulse, the waveform of said stimulus current comprising a series of said spaced pulses of one polarity followed by an equal number of said spaced pulses of opposite polarity whereby the sum of all the electrical charge transferred through each electrode is approximately zero at the end of a stimulating current waveform.

2. The improvement of claim 1, wherein said controlling means causes delivery of said spaced current pulses to bipolar pairs of said electrodes whereby the electrical stimulation caused by said electrodes is substantially simultaneous, said controlling means causing said spaced pulses to be delivered cyclically such that said spaced pulses are delivered to one electrode during the zero current periods of the spaced pulses delivered to another electrode pair.

3. The improvement of claim 2, wherein said controlling means controls the duration of each zero current interval to be at least twice the duration of each spaced pulse.

4. In a receiver-stimulator for a hearing prosthesis comprising means for receiving a transmitted data signal, means for decoding the received signal, means for generating and delivering several initial independent current signals to a selected subset of stimulating electrodes, configured as a number of bipolar pairs, according to the decoded information, the improvement comprising, means for controlling said current signals to cause said bipolar pairs to receive a series of short constant-current pulses each separated by zero-current intervals longer than each initial pulse, said series of spaced pules being divided into a first series of said current pulses having a first current direction and a second series of said current pulses having the opposite current direction whereby the sum of the charge transferred through each of the selected bipolar electrode pairs is substantially zero when the delivery of the current signals is complete.

5. The improvement of claim 2 or 4, wherein said current control means includes first switch means for defining each pulse and second switch means for defining the direction of said current pulses through each electrode pair, said second switch means being controlled so that an equal and opposite number of elemental pulses are delivered to each electrode pair.

6. The improvement of claim 1 or 4, wherein said current control means includes a voltage regulator including a voltage controlled oscillator, a phase comparator, an amplifier and capacitor means for setting the regulated voltage to a predetermined level, said phase comparator being connected to compare the output from said voltage controlled oscillator and a reference signal derived from the received signal, the output from said phase comparator being connected to the voltage controlled oscillator thereby phase-locking the voltage controlled oscillator to the received signal to ensure that the voltage output is regulated at a predetermined level.

7. The improvement of claim 6, wherein a further phase comparator is connected to compare the output from said voltage controlled oscillator and said reference signal and operates to disable the stimulating currents in the event that the voltage controlled oscillator is not phase-locked to said reference signal.

8. The improvement of claim 1 or 4, further comprising a transmitter for transmitting data concerning the stimulating current waveforms to enable the device to be tested while in a stimulating state.

* * * * *